United States Patent [19]

Vignau et al.

[11] 4,328,225
[45] May 4, 1982

[54] NOVEL 7-(2-AMINO-4-THIAZOLYL)-ACETAMIDO-CEPHALOSPORANIC ACIDS

[75] Inventors: Michel Vignau, Neuilly-sur-Seine; René Heymés, Romainville, both of France

[73] Assignee: Roussel Uclaf, Paris, France

[21] Appl. No.: 167,449

[22] Filed: Jul. 10, 1980

[30] Foreign Application Priority Data

Jul. 19, 1979 [FR] France .................. 79 18702

[51] Int. Cl.³ .......................................... A61K 31/545
[52] U.S. Cl. ..................................... 424/246; 544/22; 544/26; 544/27; 544/28
[58] Field of Search .................... 544/27, 28, 22, 26; 424/246

[56] References Cited

U.S. PATENT DOCUMENTS

| | | | |
|---|---|---|---|
| 3,839,329 | 10/1974 | Breuer et al. | 544/29 |
| 3,907,789 | 9/1975 | Wei | 544/29 |
| 3,925,370 | 12/1975 | Wei et al. | 544/29 |
| 4,152,432 | 5/1979 | Heymés et al. | 544/28 |
| 4,166,115 | 8/1979 | Takaya et al. | 424/246 |
| 4,172,942 | 10/1979 | Nudelman et al. | 544/28 |
| 4,180,661 | 12/1979 | Haviv et al. | 544/28 |
| 4,260,747 | 4/1981 | Heymes et al. | 544/28 |
| 4,278,793 | 7/1981 | Durckheimer et al. | 544/28 |

*Primary Examiner*—Paul M. Coughlan, Jr.
*Attorney, Agent, or Firm*—Hammond & Littell, Weissenberger and Muserlian

[57] ABSTRACT

Novel syn isomers of 7-(2-amino-4-thiazolyl)-acetamido-cephalosporanic acid compounds of the formula

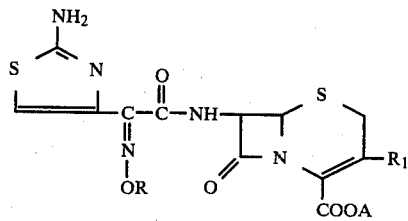

wherein R is selected from the group consisting of $-(CH_2)_n-S-R_2$, $-CHF_2$ and $-(CH_2)_n-S-CN$, $R_2$ is selected from the group consisting of optionally protonated

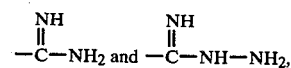

n is an integer from 1 to 4, $R_1$ is selected from the group consisting of hydrogen, chlorine, methoxy, alkyl and alkylthio of 1 to 5 carbon atoms, cycloalkyl of 3 to 5 carbon atoms, azidomethyl, acetoxymethyl, carbamoyloxymethyl,

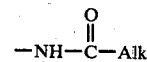

and $-CH_2-S-R'$, Alk is alkyl of 1 to 4 carbon atoms, R' is selected from the group consisting of an optionally substituted nitrogen containing heterocycle and an acyl of an aliphatic acid of 2 to 4 carbon atoms, A is selected from the group consisting of hydrogen and an easily cleavable ester and when R is $-(CH_2)_n-SR_2$, the COOA group may be the anion $-COO^-$ and when R is $-(CH_2)_n-SCN$ or $-CHF_2$, A may further be selected from the group consisting of an equivalent of an alkali metal, an alkaline earth metal, magnesium, $-NH_4$ and a non-toxic, pharmaceutically acceptable organic amine and their non-toxic, pharmaceutically acceptable acid addition salts having antibiotic properties and a novel process and novel intermediates for their preparation.

15 Claims, No Drawings

NOVEL 7-(2-AMINO-4-THIAZOLYL)-ACETAMIDO-CEPHALOSPORANIC ACIDS

STATE OF THE ART 7-(2-amino-4-thiazolyl)-acetamido-cephalosporanic acid derivatives in their syn isomer form are described in French Pat. Nos. 2,348,219; 2,137,899; and 2,385,722 as antibiotics but not of the structure of formula I.

OBJECTS OF THE INVENTION

It is an object of the invention to provide the novel cephalosporanic acid derivatives of formula I and novel processes and intermediates for their preparation.

It is another object of the invention to provide novel antibiotic compositions and a novel method of combatting bacterial infections in warm-blooded animals.

These and other objects and advantages of the invention will become obvious from the following detailed description.

THE INVENTION

The novel compounds of the invention are selected from the group consisting of syn isomers of compounds of the formula

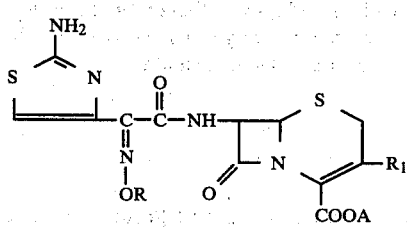

wherein R is selected from the group consisting of $-(CH_2)_n-S-R_2$, $-CHF_2$ and $-(CH_2)_n-S-CN$, $R_2$ is selected from the group consisting of optionally protonated

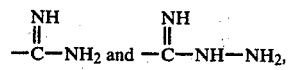

n is an integer from 1 to 4, $R_1$ is selected from the group consisting of hydrogen, chlorine, methoxy, alkyl and alkylthio of 1 to 5 carbon atoms, cycloalkyl of 3 to 5 carbon atoms, azidomethyl, acetoxymethyl, carbamoyloxymethyl,

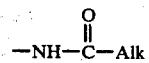

and $-CH_2-S-R'$, Alk is alkyl of 1 to 4 carbon atoms, R' is selected from the group consisting of an optionally substituted nitrogen containing heterocycle and an acyl of an aliphatic acid of 2 to 4 carbon atoms, A is selected from the group consisting of hydrogen and an easily cleavable ester and when R is $-(CH_2)_n-SR_2$, the group COOA may be the anion $-COO^-$ and when R is $-(CH_2)_n-SCN$ or $-CHF_2$, A may further be selected from the group consisting of an equivalent of an alkali metal, an alkaline earth metal, magnesium, $-NH_4$ and a non-toxic, pharmaceutically acceptable organic amine and their non-toxic, pharmaceutically acceptable acid addition salts.

Examples of groups of $R_1$ are hydrogen, alkyl of 1 to 5 carbon atoms such as methyl, ethyl, propyl, isopropyl, butyl, isobutyl, tert-butyl, pentyl, sec-pentyl and tert-pentyl, alkylthio of 1 to 5 carbon atoms such as methylthio, ethylthio, propylthio, isopropylthio, butylthio, tert.-butylthio and isobutylthio, cycloalkyl of 3 to 5 carbon atoms such as cyclopropyl, cyclobutyl and cyclopentyl, $-CH_2-S-R'$ wherein R' is 1,2,3-thiadiazolyl, 1,2,5-thiadiazolyl, 1,2,4-thiadiazolyl, 1,3,4-thiadiazolyl, 1-H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl which heterocycle may be substituted with at least one member of the group consisting of methyl, ethyl, propyl, isopropyl, methoxy, ethoxy, propoxy, isopropoxy, amino, hydroxycarbonylmethyl, dimethylaminoethyl and diethylaminoethyl, acyl of 2 to 4 carbon atoms such as acetyl, propionyl and butyryl, acylamido of 2 to 5 carbon atoms such as acetamido, propionylamido, butyrylamido, isobutyrylamido and valerylamido, chloro, methoxy or azidomethyl.

Examples of easily cleavable esters are esters wherein A is methoxymethyl, ethoxymethyl, isopropoxymethyl, α-methoxyethyl, α-ethoxyethyl, methylthiomethyl, ethylthiomethyl, isopropylthiomethyl, pivaloyloxymethyl, isovaleryloxymethyl, acetoxymethyl, propionyloxymethyl, isobutyryloxymethyl, propionyloxyethyl, isovaleryloxyethyl, 1-acetoxyethyl, 1-acetoxypropyl, 1-acetoxybutyl, 1-acetoxyhexyl and 1-acetoxyheptyl.

Examples of suitable salts for A are alkali metals such as sodium, lithium and potassium, alkaline earth metals such as calcium, magnesium, $-NH_4$ and non-toxic, pharmaceutically acceptable organic amines such as triethylamine, diethylamine, triethylamine, methylamine, propylamine, N,N-dimethyl-ethanolamine, tris(-hydroxymethyl)-aminomethane, ethanolamine, pyridine, picoline, morpholine, benzylamine, procaine, lysine, arginine, histidine and N-methylglucamine, dicyclohexylamine, N',N'-dibenzylethylenediamine.

The compounds of formula I may be in the form of non-toxic, pharmaceutically acceptable acid addition salts as they contain a salifiable amino group and examples of suitable acids are organic acids such as acetic acid, trifluoroacetic acid, maleic acid, tartaric acid, methanesulfonic acid, benzenesulfonic acid and p-toluenesulfonic acid and inorganic acids such as hydrochloric acid, hydrobromic acid, hydroiodic acid, sulfuric acid and phosphoric acid.

Among the preferred compounds of formula I are those wherein $R_1$ is hydrogen, wherein $R_1$ is $-CH_2-SR''$ and R'' is 1-methyl-1-(H)-tetrazolyl or 2-methyl-1,3,4-thiadiazolyl, wherein $R_1$ is acetoxymethyl and wherein $R_1$ is azidomethyl and their non-toxic, pharmaceutically acceptable acid addition salts.

Also among the preferred compounds of formula I are those wherein R is

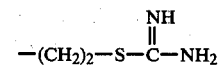

or in the optionally protonated form, wherein R is $-CHF_2$ and $R_1$ is hydrogen, 1-methyl-1-(H)-tetrazolylthiomethyl, 2-methyl-1,3,4-thiadiazolylthiomethyl, acetoxymethyl or azidomethyl.

Specific preferred compounds of the syn isomers of formula I are the syn isomer of 3-acetoxymethyl-7-[2-(2-amino-4-thiazolyl)-2-(2-aminoiminomethylthioethoxyimino)-acetamido]-ceph-3-eme-4-carboxylic acid in the form of its internal salt or its easily cleavable esters or its non-toxic, pharmaceutically acceptable acid addition salts and the syn isomer of 3-acetoxymethyl-7-[2-(2-amino-4-thiazolyl)-2-difluoromethoxyimino-acetamido]-ceph-3-eme-4-carboxylic acid and its easily cleavable esters and its alkali metal, alkaline earth metal, magnesium, ammonium and organic amine salts and its non-toxic, pharmaceutically acceptable acid addition salts.

The compounds of the invention may exist in the form of formula I or in the form of the formula

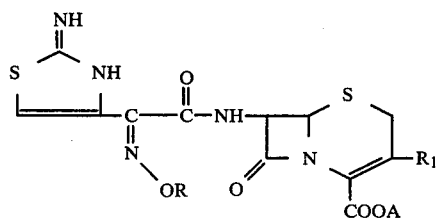

The novel process of the invention for the preparation of compounds of formula I wherein R is —$CHF_2$ comprises reacting a compound of the formula

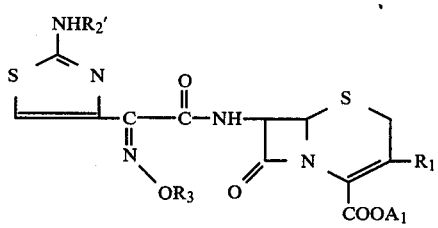

wherein $R'_2$ is selected from the group consisting of hydrogen and an amino protective group, $A_1$ is selected from the group consisting of hydrogen and an easily cleavable ester, $R_3$ is hydrogen and $R_1$ has the above definition with a compound of the formula Hal-1—$CHF_2$ wherein $Hal_1$ is chlorine or bromine to obtain a compound of the formula

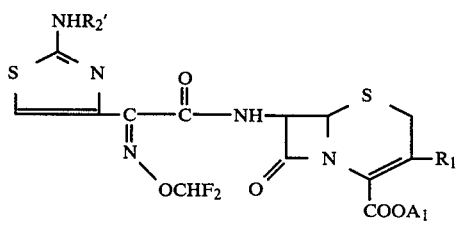

and optionally esterifying or salifying the latter if $R'_2$ and $A_1$ are hydrogen to obtain the corresponding compounds of formula I or wherein $R'_2$ is an amino protective group, and $A_1$ is an easily cleavable ester subjecting the latter to at least one agent selected from the group consisting of thiourea, hydrolysis agent and hydrogenolysis agent to obtain the corresponding compound of the formula

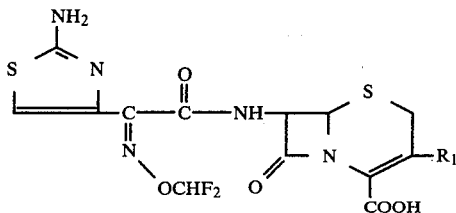

which may optionally be esterified or salified with a base or an acid.

The process of the invention for the preparation of a compound of formula I wherein R is —$(CH_2)_n$—$SR_2$ or —$(CH_2)_n$—SCN comprises reacting a compound of the formula

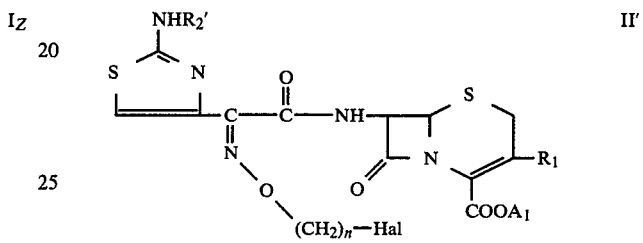

wherein $R_1$, $R'_2$ and $A_1$ have the above definitions, Hal is a halogen and n is an integer from 1 to 4 with thiourea or with a compound of the formula

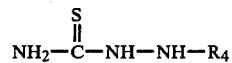

wherein $R_4$ is a protective amino group or with a compound of the formula NC—S—$R_5$ wherein $R_5$ is selected from the group consisting of —$NH_4$ and an alkali metal to obtain a compound of the formula

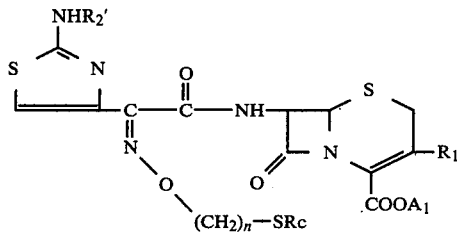

wherein Rc is selected from the group consisting of

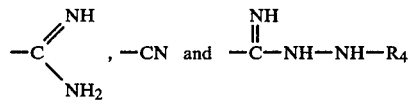

and are compounds of formula I when $R'_2$ and $A_1$ are hydrogen and Rc is —CN or

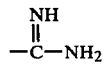

and optionally esterifying or salifying the latter compounds and when $R'_2$ or $A_1$ are other than hydrogen and Rc is

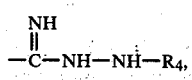

treating the latter with at least one agent selected from the group consisting of thiourea, hydrolysis agent and hydrogenolysis agent to obtain a compound of the formula

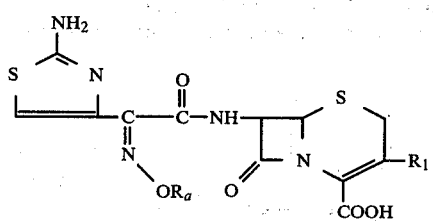

wherein Ra is selected from the group consisting of $-(CH_2)_n-SR_2$ and $-(CH_2)_n-SCN$ which are compounds of formula I which may be esterified or salified with a base or an acid.

Examples of the protective amino group of the compounds of formulae II and II' are those wherein $R'_2$ is selected from the group consisting of alkyl of 1 to 6 carbon atoms such as tert.-butyl or tert.-amyl, aliphatic acyl, aromatic acyl, heterocyclic, a carbamoyl, aryllloweralkyl and haloalkyl.

Examples of aliphatic acyls are lower alkanoyl such as formyl, acetyl, propionyl, butyryl, isobutyryl, valeryl, isovaleryl, oxalyl, succinyl and pivaloyl, lower alkoxy carbonyl and cycloalkoxycarbonyl such as methoxycarbonyl, ethoxycarbonyl, propoxycarbonyl, 1-cyclopropylethoxycarbonyl, isopropoxycarbonyl, butoxycarbonyl, tert.-butoxycarbonyl, pentyloxycarbonyl, tert.-pentyloxycarbonyl and hexyloxycarbonyl.

Examples of aromatic acyl groups are benzoyl, toluoyl, naphthoyl, phthaloyl, mesyl, phenylacetyl and phenylpropionyl and arylalkoxycarbonyl such as benzyloxycarbonyl. The aliphatic acyl and aromatic acyl groups may also be substituted with at least one member of the group consisting of chlorine, fluorine, bromine and iodine and examples thereof are chloroacetyl, dichloroacetyl, trichloroacetyl, trifluoroacetyl and bromoacetyl.

The group $R'_2$ may also be optionally substituted aryl lower alkyl such as benzyl, 4-methoxybenzyl, phenethyl, trityl, 3,4-dimethoxybenzyl and benzhydryl, haloloweralkyl such as trichloroethyl, a carbamoyl such as methylcarbamoyl, phenylcarbamoyl, naphthylcarbamoyl and the corresponding thiocarbamoyls as well as chlorobenzoyl, p-nitrobenzoyl, p-tert.-butyl-benzoyl, phenoxyacetyl, caprylyl, n-decanoyl and acryloyl. The said list of protective groups is not intended to be exhaustive and may include other groups such as those used in peptide chemistry.

Examples of easily cleavable esters of $A_1$ are lower alkyl esters such as butyl, isobutyl, tert.-butyl, pentyl and hexyl, other ester groups such as acetoxymethyl, propionyloxymethyl, butyryloxymethyl, valeryloxymethyl, pivaloyloxymethyl, 2-acetoxyethyl, 2-propionyloxyethyl, 2-butyryloxyethyl, 2-mesylethyl, 2-iodoethyl, $\beta,\beta,\beta$-trichloroethyl, vinyl, allyl, ethynyl, propynyl, benzyl, 4-methoxybenzyl, 4-nitrobenzyl, phenethyl, trityl, diphenylmethyl and 3,4-dimethoxy- benzyl as well as phenyl, 4-chlorophenyl, tolyl and tert.-butylphenyl.

The Hal is preferably bromine or iodine. The protective group $R_4$ may be the same as $R'_2$ discussed above.

The reaction of a compound of formula II with the compound of the formula $Hal_1-CHF_2$ is effected in the presence of a base such as sodium hydroxide, potassium hydroxide, sodium carbonate, sodium bicarbonate, potassium carbonate or potassium bicarbonate in an organic solvent such as anhydrous ethanol, dioxane, methanol, isopropanol, tetrahydrofuran or mixtures of said solvents.

The reaction of the compound of formula II' with thiourea or $NC-S-R_5$ or

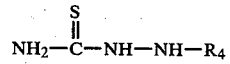

is preferably effected in an organic solvent such as chloroform, hexamethylphosphorotriamide, dimethylformamide, acetone or dioxane optionally in the presence of a base. In the absence of a base, the product is the hydrohalide corresponding to the halogen of Hal.

The removal of the easily removable groups of $R'_2$ and $A_1$ and $R_4$ may be effected by acid hydrolysis or by basic hydrolysis or with hydrazine.

Acid hydrolysis is preferred to eliminate optionally substituted alkoxycarbonyl or cycloalkoxycarbonyl groups such as tert.-pentyloxycarbonyl or tert.-butoxycarbonyl and optionally substituted arylalkoxycarbonyl groups such as benzyloxycarbonyl, trityl, tert.-butyl or 4-methoxy-benzyl. The acid may be an organic or inorganic acid and is preferably selected from the group consisting of hydrochloric acid, benzene sulfonic acid, p-toluene sulfonic acid, formic acid and trifluoroacetic acid.

Basic hydrolysis is preferred for the removal of acyl groups such as trifluoroacetyl and the preferred base is an alkali metal hydroxide such as potassium hydroxide and sodium hydroxide. Equally useful, however, are other bases such as magnesium hydroxide, baryta or alkali metal carbonates or bicarbonates such as sodium or potassium carbonates or bicarbonates and sodium acetate or potassium acetate.

The hydrolysis with hydrazine is preferably used to remove groups such as phthaloyl. The groups $R'_2$ and $R_4$ may also be removed with a zinc-acetic acid system for groups such as trichloroethyl. Benzhydryl and benzyloxycarbonyl are preferably removed by hydrogen in the presence of a catalyst. Chloroacetyl is preferably removed with thiourea in acidic or neutral media as described by Masaki [JACS., Vol. 90 (1968), p. 4508]. Other known methods of removing the amino protective groups may also be used.

The process of the invention is preferred with the compounds wherein $R'_2$ is selected from the group consisting of trityl, chloroacetyl, tert.-pentyloxycarbonyl, tert.-butoxycarbonyl and benzyloxycarbonyl.

The removal of the groups when $A_1$ is other than hydrogen may be the same as discussed for the removal of groups $R'_2$ and $R_4$ and the hydrolysis may be acidic or basic. Acid hydrolysis is preferred to remove optionally substituted alkyl and optionally substituted aralkyl groups. The preferred acids are hydrochloric acid, formic acid, p-toluene sulfonic acid and trifluoroacetic acid. Other groups of $A_1$ can be removed by known procedures. The preferred reaction conditions are moderate and are effected at room temperature or with slight heating.

In the above processes, a portion of the products obtained are ceph-2-eme products which can be transformed into the corresponding ceph-3-eme compounds by oxidizing the product containing ceph-2-eme compounds to the corresponding sulfoxide, preferably with a peracid such as m-chloroperbenzoic acid, transforming the $\Delta_2$-sulfoxide in the presence of water or a hydroxylated solvent to the $\Delta_3$-sulfoxide such as described by Kaiser et al. [J. Org., Vol. 35 (1970) p. 2430], Spry et al. [J. Org., Vol. 40 (1975), p. 2411] or U.S. Pat. No. 3,705,897 or German Pat. No. 1,937,016 and reducing the $\Delta_3$-sulfoxide in the presence of a hydrogen halide or phosphorus trichloride.

The salification of the free acids of formula I may be effected in known ways. For example, the acids or a solvate thereof such as an ethanol solvate or a hydrate of the acid may be reacted with a mineral base such as sodium hydroxide, potassium hydroxide, sodium carbonate, potassium carbonate, sodium bicarbonate or potassium bicarbonate or with salts of mineral acids such as trisodium phosphate and salts of organic acids.

Such organic acid salts are alkali metal salts such as sodium salts of optionally unsaturated aliphatic carboxylic acids of 1 to 18, preferably 2 to 10, carbon atoms in which the aliphatic group may be interrupted with at least one heteroatom such as oxygen or sulfur or substituted with aryl groups such as phenyl, thienyl or furyl or with at least one —OH or at least one halogen such as fluorine, chlorine or bromine, preferably chlorine or with at least one carboxylic group or lower alkoxycarbonyl, preferably methoxycarbonyl, ethoxycarbonyl or propoxycarbonyl or with at least one aryloxy such as phenoxy. When aromatic acids are used as the organic acid, it is preferred to use substituted benzoic acids such as lower alkyl benzoic acids to ensure sufficient solubility.

Examples of specific organic acids are formic acid, acetic acid, acrylic acid, butyric acid, adipic acid, isobutyric acid, n-caproic acid, isocaproic acid, chloropropionic acid, crotonic acid, phenylacetic acid, 2-thienylacetic acid, 3-thienylacetic acid, 4-ethylphenylacetic acid, glutaric acid, monoethyl adipate, hexanoic acid, heptanoic acids, decanoic acids, oleic acid, stearic acid, palmitic acid, 3-hydroxypropionic acid, 3-methoxypropionic acid, 3-methylthiobutyric acid, 4-chlorobutyric acid, 4-phenylbutyric acid, 3-phenoxybutyric acid, 4-ethyl-benzoic acid and 1-propyl benzoic acid. The preferred salt of an organic acid is sodium acetate, sodium diethylacetate and sodium 2-ethylhexanoate.

The salification of the acid of formula I may also be effected with an organic base such as diethylamine, trimethylamine, triethylamine, propylamine, N,N-dimethyl-ethanolamine, tris (hydroxymethyl)-aminomethane, arginine, lysine, methylamine, ethanolamine, pyridine, picoline, dicyclohexylamine, procaine, histidine, N-methyl-glucamine, morpholine or benzylamine.

The salification may be effected in a solvent or a mixture of solvents such as water, ether, methanol, ethanol or acetone.

The salts may be crystalline or amorphous depending upon the reaction conditions used. Crystalline salts are prepared preferably by reacting the free acid with salts of aliphatic carboxylic acids, preferably sodium acetate.

The non-toxic, pharmaceutically acceptable acid addition salts of the compounds of formula I may be made by known methods by reacting them with a mineral or organic acid.

The esterification of the free acids of formula I may be effected by classical conditions, for example, by reacting the free acid with a compound of the formula $Z-R_6$ wherein Z is —OH or a halogen such as fluorine, chlorine, bromine or iodine and $R_6$ is the ester group to be introduced.

A modification of the process of the invention for the preparation of a compound of formula I wherein R is —CHF$_2$ comprises reacting a compound of the formula

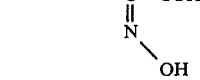

wherein $R'_2$ has the above definition with a compound of the formula $Hal_1$—CHF$_2$ wherein $Hal_1$ has the above definition to obtain a compound of the formula

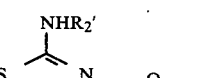

and reacting the latter or a functional acid derivative thereof with a compound of the formula

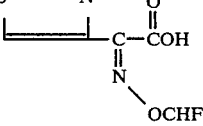

wherein $A_1$ and $R_1$ have the above definition to obtain the corresponding compound of formula III which may then be reacted to form the compounds of formula I.

To obtain a compound of formula I wherein R is —(CH$_2$)$_n$—SR$_2$ or —(CH$_2$)$_n$—SCN, a compound of the formula

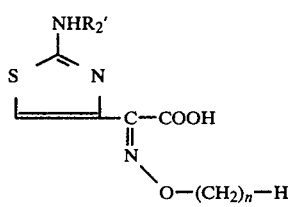

wherein $R'_2$, Hal and n have the above definition is reacted with thiourea or a compound of formula

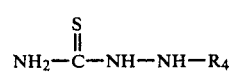

or a compound of the formula NC—S—R₅ wherein R₄ and R₅ have the above definition to obtain a compound of the formula

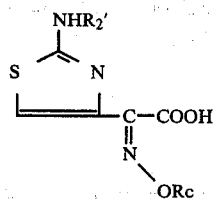     V' wherein R'₂ and Rc have the above definition and reacting the latter or an functional acid derivative thereof with a compound of formula VI to obtain the corresponding compound of formula III' and may then be reacted to form the compounds of formula I.

The first step of the above 2 processes are effected under the same reaction conditions as indicated previous for the reaction of the products of formulae II and II'.

The functional derivatives of the acids of formula V or V' may be the acid halide, symetrical acid anhydride, mixed acid anhydride, amide or active ester. An example of a mixed acid anhydride is formed with isobutyl chloroformate or tosyl chloride and the acid halide is preferably the acid bromide or acid chloride. Examples of active esters are esters of 2,4-dinitrophenol or 1-hydroxy-benzo [1] triazole. Also useful are the acid amide or azide. The acid anhydride may be prepared in situ by reaction with N,N-disubstituted-diimides such as N,N-dicyclohexylcarbodiimide.

The acylation reaction is preferably effected in an organic solvent such as methylene chloride but other solvents such as tetrahydrofuran, chloroform or dimethylformamide may be used. When the acid halide or the mixed anhydride formed with isobutyl chloroformate is used, the acylation is preferably effected in the presence of a base such as sodium hydroxide, potassium hydroxide, sodium and potassium carbonates and bicarbonates, sodium acetate, triethylamine, pyridine, morpholine or N-methylmorpholine. The reaction temperature is generally room temperature or below.

In the modifications of the process, R'₂ is preferably trityl, chloroacetyl, tert.-pentyloxycarbonyl, tert.-butoxycarbonyl or benzyloxycarbonyl.

The compounds of formula II wherein R₃ is hydrogen may be prepared by reacting a compound of the formula

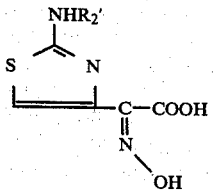     A which is described in French Pat. No. 2,383,188 with 2-methoxypropene to obtain a compound of the formula

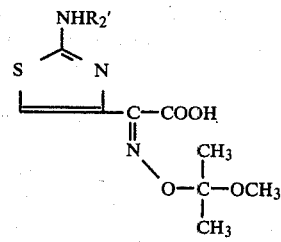

which in the form of a functional derivative such as a symetrical anhydride may be reacted with a compound of the formula

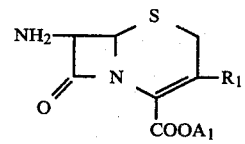

to obtain a compound of the formula

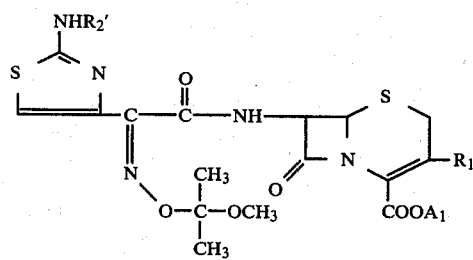

which may be treated with an aqueous mineral acid to obtain a compound of formula II wherein R₃ is hydrogen. The latter compound may be reacted with a compound of the formula Hal—$(CH_2)_n$—Hal to obtain the corresponding compound of formula II wherein R₃ is —$(CH_2)_n$—Hal.

The products of formula IV' can be obtained by reacting a compound of formula A with a compound of the formula Hal—$(CH_2)_n$—Hal. The compounds of the formula

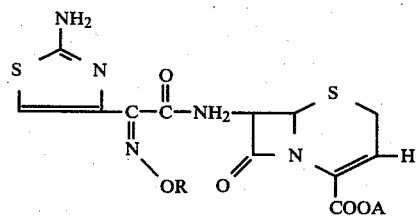

wherein A has the above definition and R is —CHF₂ or

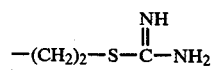

are supplementary compounds which can be prepared according to the process of the invention.

The antibiotic compositions of the invention are comprised of an antibiotically effect amount of at least one compound of formula I and its non-toxic, pharmaceutically acceptable acid addition salts and an inert pharmaceutical carrier. The compositions may be in the form of tablets, dragees, gelules, granules, suppositories, injectable solutions or suspensions, creams, pomades, gels, etc. prepared in the usual fashion.

Examples of suitable excipients or pharmaceutical carriers are talc, arabic gum, lactose, starch, magnesium stearate, cacao butter, aqueous or non-aqueous vehicles, fatty bodies of vegetable or animal origin, paraffinic derivatives, glycols, preservatives, diverse wetting agents, dispersants and emulsifers. The compositions of the invention possess very good antibiotic activity against gram positive bacteria such as staphylococcus, streptococcus, particularly penicillin resistant staphylococcus as well as against gram negative bacteria such as coliforma bacteria, Klebsiella, Salmonella, Proteus and Pseudomonas.

The compositions are therefore useful in the treatment of germ sensitive infections and particularly those of staphylococcia such as staphylococcal septicemia, staphylococcia malignant on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella, Salmonella, Pseudomonas and other infections caused by gram negative bacteria. The compositions are also useful to disinfect surgical instruments.

Among the preferred compositions of the invention are those wherein $R_1$ is hydrogen, wherein $R_1$ is —CH$_2$—SR″ and R″ is 1-methyl-1-(H)-tetrazolyl or 2-methyl-1,3,4-thiadiazolyl, wherein $R_1$ is acetoxymethyl and wherein $R_1$ is azidomethyl and their non-toxic, pharmaceutically acceptable acid addition salts.

Also among the preferred compositions of the invention are those wherein R is

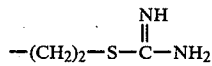

or in the optionally protonated form, wherein R is —CHF$_2$ and $R_1$ is hydrogen, 1-methyl-1-(H)-tetrazolylthiomethyl, 2-methyl-1,3,4-thiadiazolylthiomethyl, acetoxymethyl or azidomethyl.

Examples of specific preferred compositions are those wherein the active compound is the syn isomer of 3-acetoxymethyl-7-[2-(2-amino-4-thiazolyl)-2-(2-aminoiminomethylthioethoxyimino)-acetamido]-ceph-3-eme-4-carboxylic acid in the form of its internal salt or its easily cleavable esters or its non-toxic, pharmaceutically acceptable acid addition salts and the syn isomer of 3-acetoxymethyl-7-[2-(2-amino-4-thiazolyl)-2-(2-difluoromethoxyimino-acetamido]-ceph-3-eme-4-carboxylic acid and its easily cleavable esters and its alkali metal, alkaline earth metal, magnesium, ammonium and organic amine salts and its non-toxic, pharmaceutically acceptable acid addition salts.

The novel method of the invention for combatting bacterial infections in warm-blooded animals, including humans, comprises administering to warm-blooded animals an antibacterially effective amount of at least one compound of formula I and its non-toxic pharmaceutically acceptable acid and addition salts. The compounds may be administered orally, rectally, parenterally or locally by topical application to the skin or mucous. The usual daily dose is depending on the compound, the complaint concerned, the subject treated and the method of administration. It may be, daily, 5 to 80 mg/kg by oral route in the adult with the product of example 1 or 9, or 10 to 20 mg/kg three times daily by intramuscular route.

The novel intermediate of the invention are the syn isomers of the formulae

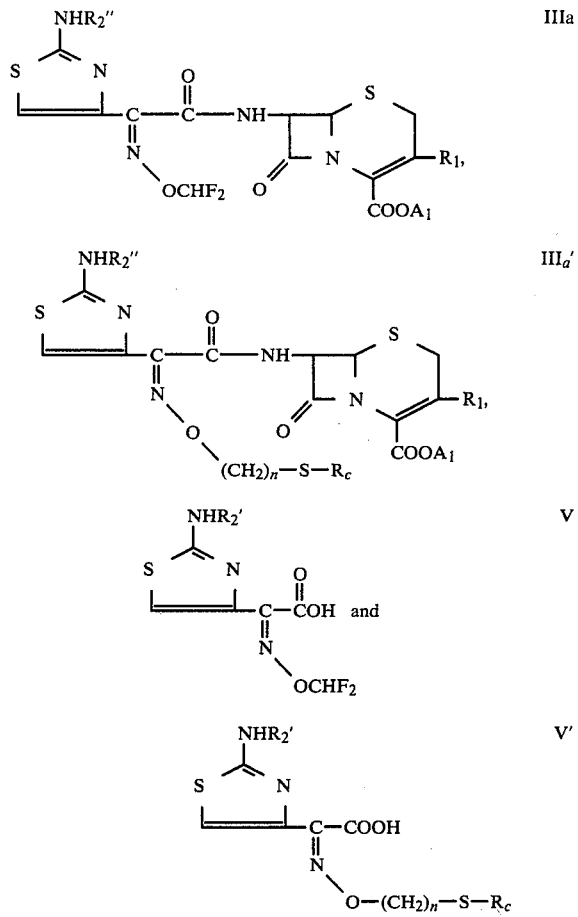

wherein $R'_2$, $R_1$, $A_1$, n and $R_c$ have the above definitions and $R_2″$ is an amine protective group.

In the following examples there are described several preferred embodiments to illustrate the invention. However, it is to be understood that the invention is not intended to be limited to the specific embodiments.

EXAMPLE 1

Trifluoroacetate of the syn isomer of 3-acetoxymethyl-7-[2-(2-amino-4-thiazolyl)-2-(2-aminoiminomethylthio-ethoxyimino)-acetamido]-ceph-3-eme-4-carboxylic acid STEP A: Internal salt of the syn isomer of 2-(2-tritylamino-4-thiazolyl)-2-(2-amino-iminomethylthio-ethoxy)-imino-acetic acid A mixture of 4.6 g of the syn isomer of 2-(2-iodoethoxy)-imino-2-(2-tritylamino-4-thiazolyl)-acetic acid (prepared by Example 1 of Belgium Pat. No. 875,217) solvated with dichloroethane, 1 g of thiourea and 20 ml of hexamethylphosphortriamide was stirred at room temperature in the dark for 27 hours and was then poured into 320 ml of isopropyl ether. The gummy precipitate was taken up in isopropyl ether and then in water and the mixture was vacuum filtered. The recovered product was dried to obtain 3.59 g of internal salt of the syn isomer of 2-(2-tritylamino-4-thiazolyl)-2-(2-amino-iminomethylthio-ethoxy)imino-acetic acid melting at 260° C.

NMR Spectrum (CF$_3$COOD): triplet centered at 3.57 ppm J=6 Hz (—CH$_2$—S—); triplet centered at 4.72 ppm J=6 Hz (—N—O—CH$_2$—).

STEP B: Syn isomer of benzhydryl 3-acetoxymethyl-7-[2-(2-tritylamino-4-thiazolyl]-2-(2-aminoiminomethyl-thioethoxyimino)-acetamido-ceph-3-eme-4-carboxylate hydroiodide A mixture of 10.63 g of the product of Step A, 4.14 g of pyridine hydroiodide, 8.24 g of dicyclohexylcarbodiimide, 7 g of benzhydryl 3-acetoxymethyl-7-amino-ceph-3-eme-4-carboxylate and 60 ml of anhydrous dimethylformamide was stirred at 15° C. for 25 minutes and then 10 minutes at room temperature and was then vacuum filtered. The filter was washed with methylene chloride and the methylene chloride was evaporated from the filtrate at a maximum of 45° C. under reduced pressure. The filtrate was then poured into one liter of isopropyl ether and was stirred for 20 minutes. The mixture was decanted and the surnagent was taken away. The precipitate was taken up in isopropyl ether and the suspension was stirred for 20 minutes and was decanted. The insolubles were dissolved in methanol and ether was added to the solution to cause precipitation. The mixture was stirred for 70 minutes and was vacuum filtered and the recovered product was rinsed with ether and dried to obtain 18.2 g of syn isomer of benzhydryl 3-acetoxymethyl-7-[2-(2-tritylamino-4-thiazolyl]-2-(2-aminoiminomethylthioethoxyimino)-acetamido-ceph-3-eme-4-carboxylate hydroiodide melting at ≃194° C. (with decomposition).

STEP C: Trifluoroacetate of the syn isomer of 3-acetoxymethyl-7-[2-(2-amino-4-thiazolyl)-2-(2-aminoiminomethylthioethoxyimino)-acetamido]-ceph-3-eme-4-carboxylic acid A mixture of 7.5 g of the product of Step B and 75 g of trifluoroacetic acid was stirred at room temperature for 3 minutes and was then vacuum filtered. The filtrate was added to 1.2 liters of iced ether and after standing at room temperature for 15 minutes, the mixture was vacuum filtered. The recovered product was dissolved in methanol and ether was added to the solution to cause precipitation. The mixture was stirred for 15 minutes and was then vacuum filtered and the recovered product was rinsed with ether and dried to obtain 2.19 g of trifluoroacetate of the syn isomer of 3-acetoxymethyl-7-[2-(2-amino-4-thiazolyl)-2-(2-aminoinomethylthioethoxyimino)-acetamido]-ceph-3-eme-4-carboxylate acid melting at 256° C. (decomposition).

NMR Spectrum (C$_2$D$_3$)$_2$SO: 2.02 ppm singulet (—OAc); 4.25 ppm (N—O—CH$_2$—); 6.78 ppm singulet (5-hydrogen of thiazole).

IR Spectrum (nujol): Absorption at 1768 cm$^{-1}$ (β-lactam); at 1538 cm$^{-1}$ (amide II+heterocycle)

UV Spectrum (N/10 HCl in ethanol): max. at 262 nm: E$_1^1$=291.

EXAMPLE 2

Trifluoroacetate of the syn isomer of
3-acetoxymethyl-7-[2-(2-amino-4-thiazolyl)-2-(2-aminoiminomethylthioethoxyimino)-acetamido]-ceph-3-eme-4-carboxylic acid STEP A: Syn isomer of benzhydryl 3-acetoxymethyl-7-[2-(2-tritylamino-4-thiazolyl)-2-(2-aminoiminomethyl-thioethoxyimino)-acetamido]-ceph-3-eme-4-carboxylate hydroiodide A mixture of 870 mg of the syn isomer of benzhydryl 3-acetoxymethyl-7-[2-(2-tritylamino-4-thiazolyl)-2-(2-iodoethoxyimino)-acetamido]-ceph-3-eme-4-carboxylate [described in Belgium Pat. No. 875,217], 131 mg of thiourea and 1.7 ml of anhydrous hexamethylphosphorotriamide was stirred for 32 hours and 75 ml of isopropyl ether were added thereto with stirring. The mixture was decanted and 45 ml of ethyl ether were added thereto. The mixture was vacuum filtered to obtain 1.229 g of solvated syn isomer of benzhydryl 3-acetoxymethyl-7-[2-(2-tritylamino-4-thiazolyl)-2-(2-aminoiminomethylthioethoxyimino)-acetamido]-ceph-3-eme-4-carboxylate hydroiodide melting at ≃100° C.

NMR Spectrum (CDCl$_3$): Peaks at 2.0 ppm singulet (—OAc); at 3.33 to 3.83 ppm (—CH$_2$—S—); at 4.5 ppm (—OCH$_2$—); at 4.88 to 4.98 ppm (C$\underline{H}_2$OAc); at 5.14 ppm doublet J=5 Hz (6-hydrogen); at 5.83–6.08 ppm (7-hydrogen); at 6.78 ppm singulet (5-hydrogen-syn thiazole).

STEP B: Trifluoroacetate of syn isomer of 3-acetoxymethyl-7-[2-(2-amino-4-thiazolyl)-2-(2-aminoiminomethylthioethoxyimino)-acetamido]-ceph-3-eme-4-carboxylic acid A mixture of 450 mg of the product of Step A and 4.5 ml of trifluoroacetic acid was stirred at room temperature for 3 minutes and was then vacuum filtered. The filtrate was added to 45 ml of iced ether and the mixture was stirred for 15 minutes and was then vacuum filtered. The filter was rinsed with ether and the recovered product was taken up in 0.8 ml of methanol and 8 ml of ether were added to the mixture. The mixture was stirred for 15 minutes and was vacuum filtered. The product was rinsed with ether and dried to obtain 100 mg of trifluoroacetate of syn isomer of 3-acetoxymethyl-7-[2-(2-amino-4-thiazolyl)-2-(2-aminoiminoethylthioethoxyimino)-acetamido]-ceph-3-eme-4-carboxylic acid melting at 256°–258° C. (with decomposition).

NMR Spectrum (CD$_3$)$_2$SO: Peaks at 2.02 ppm singulet (—OAc); at 6.77 ppm singulet (5-proton of thiazole).

IR Spectrum (nujol): Absorption at 1769 cm$^{-1}$ (β-lactam); at 1534 cm$^{-1}$ (amide II+heterocycle).

UV Spectrum (N/10 HCl in ethanol): max. at 259 nm: E$_1^1$=327.

EXAMPLE 3

Syn isomer of
3-acetoxymethyl-7-[2-(2-amino-4-thiazolyl)-2-(2-aminoiminomethylthioethoxyimino)-acetamido]-ceph-3-eme-4-carboxylic acid hydroiodide A mixture of 130 mg of the trifluoroacetate of the syn isomer of 3-acetoxymethyl-7-[2-(2-amino-4-thiazolyl)-2-(2-iodomethoxyimino)-acetamido]-ceph-3-eme-4-carboxylic acid [described in Belgium Pat. No. 875,217], 28 mg of thiourea and 0.37 ml of dimethylformamide was stirred for 36½ hours at room temperature and 3 ml of isopropyl ether were added thereto to effect precipitation. The mixture was decanted and the gummy residue was taken up in isopropyl ether. The ethyl ether followed by ethyl acetate were added thereto and the mixture was vacuum filtered. The recovered product was washed with ethyl acetate and dried to obtain 113 mg of product which was crystallized from ethyl acetate to obtain 85 mg of syn isomer of 3-acetoxymethyl-7-[2-(2-amino-4-thiazolyl)-2-(2-aminoiminoethylthioethoxyimino)-acetamido]-ceph-3-eme-4-carboxylic acid hydroiodide melting at ≃250° C.

NMR Spectrum (CD$_3$)$_2$SO: Peaks at 2.02 ppm singulet (—OAc); at 4.28 ppm triplet J=6 Hz (N—O—CH$_2$—); at 5.16 ppm doublet J=5 Hz (6-hydrogen; at 5.68 to 5.88 ppm (7-hydrogen); at 6.82 ppm singulet (5-proton of thiazole).

UV Spectrum (N/10 HCl in ethanol): Max. at 220 nm: $E_1^1$=444, ε=29,800; Inflex. at 255 nm: $E_1^1$=262, ε=17,600.

EXAMPLE 4

Internal salt of the syn isomer of 3-[(1-methyl-1H-tetrazol-5-yl)-thiomethyl]-7-[2-(2-amino-4-thiazolyl)-2-(2-aminoiminomethylthioethoxyimino)-acetamido]-ceph-3-eme-4-carboxylic acid STEP A: Internal salt of the syn isomer of 3-[(1-methyl-1H-tetrazol-5-yl)-thiomethyl]-7-[2-(2-tritylamino-4-thiazolyl)-2-(2-aminoiminomethylthioethoxyimino)-acetamido]-ceph-3-eme-4-carboxylic acid A mixture of 660 mg of 3-[(1-methyl-1H-tetrazol-5-yl)-thiomethyl]-7-amino-ceph-3-eme-4-carboxylic acid and 10 ml of anhydrous dimethylformamide was stirred for 10 minutes and then was cooled to 15° C. after which 260 ml of triethylenediamine were added thereto in fractions over 5 minutes with stirring. After 3 minutes, 1.68 g of pyridine hydroiodide was rapidly added thereto and after stirring for 2 minutes, 1.06 g of 2-(2-tritylamino-4-thiazolyl)-2-(2-aminoiminomethylthioethoxyimino)-acetic acid were added thereto. The mixture was stirred at 15° C. for 5 minutes and then 840 mg of dicyclohexylcarbodiimide were added thereto all at once. The mixture was stirred for 45 minutes and was then vacuum filtered and the filtrate was poured into 250 ml of iced water. The mixture was stirred for 30 minutes and was vacuum filtered. The product was washed with water and dried to obtain 1.338 of amorphous product. A mixture of 1.23 g of the product and 10 ml of methylene chloride was stirred for 30 minutes and was then vacuum filtered. The filtrate was treated with activated carbon and was vacuum filtered. The filtrate was evaporated to dryness to obtain 857 mg of internal salt of the syn isomer of 3-[(1-methyl-1H-tetrazol-5-yl)-thiomethyl]-7-[2-(2-tritylamino-4-thiazolyl)-2-(2-aminoiminomethylthioethoxyimino)-acetamido]-ceph-3-eme-4-carboxylic acid.

NMR Spectrum (CD$_3$)$_2$SO: Peaks at 3.9 ppm (—N—CH$_3$); at 7.3 ppm (trityl protons).

IR Spectrum (CHCl$_3$): Absorption of 1769 cm$^{-1}$ (β-lactam); at 1674 cm$^{-1}$ (amide); at 1600 and 1493 cm$^{-1}$ (COO$^-$ +aromatic); at 1525 cm$^{-1}$ (amide II+-heterocycle).

UV Spectrum (N/10 HCl in ethanol): Max. at 271 nm: $E_1^1$=230.

STEP B: Internal salt of syn isomer of 3-[(1-methyl-1H-tetrazol-5-yl)-thiomethyl]-7-[2-(2-amino-4-thiazolyl)-2-(2-aminoiminomethylthioethoxyimino)-acetamido]-ceph-3-eme-4-carboxylic acid A solution of 800 mg of the product of Step A in 8 ml of 92% aqueous acetic acid was heated at 48°–50° C. for 135 minutes and was then vacuum filtered. The filtrate was added to 150 ml of isopropyl ether and the mixture was stirred for 30 minutes, let stand for one hour and was vacuum filtered. The product was washed with isopropyl ether, then with ether and dried to obtain 537 mg of product which was added to 2 ml of ethanol. The mixture was stirred for 30 minutes and the product was then stirred with 2.5 ml of water. 325 mg of the product were then added to 2 ml of acetic acid and 20 ml of methanol and 4 ml of water were added dropwise to the mixture. The mixture was stirred for 30 minutes and was vacuum filtered. The filtrate was treated with activated carbon and was vacuum filtered. The filtrate was evaporated to dryness and the residue was taken up a plurality of times in ethanol to obtain 175 mg of internal salt of syn isomer of 3-[(1-methyl-1H-tetrazol-5-yl)-thiomethyl]-7-[2-(2-amino-4-thiazolyl)-2-(2-aminoiminomethylthioethoxyimino-acetamido]-ceph-3-eme-4-carboxylic acid in the form of a white solid melting at ≃258° C.

NMR Spectrum (CD$_3$)$_2$SO: Peaks at 6.82 ppm singulet (5-proton of syn thiazol); at 3.92 ppm (—N H$_3$); at 4.33 ppm (N—OCH$_2$— and CH$_2$—S—); (6- and 7-hydrogen); at ≃5 to 5.83 ppm (hydrogen of β-lactam).

IR Spectrum (nujol): Absorption at 1766 cm$^{-1}$ (β-lactam); at 1667 cm$^{-1}$ (amide carbonyl); at 1597 cm$^{-1}$ (—COO$^-$); at 1533 cm$^{-1}$ (amide II).

UV Spectrum (N/10 HCl in ethanol): Inflex. towards 223 nm: $E_1^1$=338; max. at 263 nm: $E_1^1$=295, ε=17,700; Inflex. towards 280 nm: $E_1^1$=225.

EXAMPLE 5

Internal salt of syn isomer of 3-azidomethyl-7-[2-(2-amino-4-thiazolyl)-2-(2-aminoiminomethylthioethoxyimino)-acetamido]-ceph-3-eme-4-carboxylic acid STEP A: Internal salt of syn isomer of 3-azidomethyl-7-[2-(2-tritylamino-4-thiazolyl)-2-(2-aminoiminomethylthioethoxyimino)-acetamido]-ceph-3-eme-4-carboxylic acid A mixture of 255 mg of 3-azidomethyl-7-amino-ceph-3-eme-4-carboxylic acid and 3 ml of anhydrous formamide was stirred for 15 minutes and then 168 mg of triethylenediamine were added in fractions. 412 mg of pyridine hydroiodide were added to the resulting solution and after cooling the mixture to 15° C., 532 mg of 2-(2-tritylamino-4-thiazolyl)-2-(2-aminoiminomethylthioethoxyimino)-acetic acid, 207 mg of pyridine hydroiodide and 3 ml of dimethylformamide were added all at once to the mixture. 412 mg of dicyclohexylcarbodiimide were added to the mixture which was stirred at 15° C. for 20 minutes, at 20° C. for 40 minutes and was then vacuum filtered. 100 ml of water were added to the filtrate and the mixture was stirred for 30 minutes, let stand for 30 minutes and was then vacuum filtered. The recovered product was washed with water and dried to obtain 437 mg of raw product which was stirred with 8.6 ml of chloroform for 30 minutes. The mixture was vacuum filtered and the filtrate was treated with activated carbon and was vacuum filtered. The filtrate was evaporated to dryness to obtain 350 mg of internal salt of syn isomer of 3-azidomethyl-7-[2-(2-tritylamino-4-thiazolyl)-2-(2-aminoiminomethylthioethoxyimino)-acetamido]-ceph-3-eme-4-carboxylic acid.

IR Spectrum (CHCl$_3$): Absorption at 2160 cm$^{-1}$ (azide); at 1769 cm$^{-1}$ (β-lactam); at 1670 cm$^{-1}$ (amide); at 1600 cm$^{-1}$ (—COO$^-$); at 1521 cm$^{-1}$ (amide II).

STEP B: Internal salt of syn isomer of 3-azidomethyl-7-[2-(2-amino-4-thiazolyl)-2-(2-aminoiminomethylthioethoxyimino)-acetamido]-ceph-3-eme-4-carboxylic acid A mixture of 344 mg of the product of Step A and 3.5 ml of 92% aqueous acetic acid was heated at 46°–50° C. for 135 minutes and the solution was treated with activated carbon, heated at 46°–50° C. for 30 minutes and was vacuum filtered hot. 80 ml of ether were added to the filtrate and the mixture stood for 15 minutes and was vacuum filtered. The product was washed with ether and dried to obtain 159 mg of internal salt of syn isomer of 3-azidomethyl-7-[2-(2-amino-4-thiazolyl)-2-(2-aminoiminomethylthioethoxyimino)-acetamido]-ceph-3-eme-4-carboxylic acid melting at ≃238° C.

NMR Spectrum $(CD_3)_2SO$: Peaks at 6.8 ppm singulet (5-proton of thiazole); at 5.06 ppm doublet J=5 Hz (6-hydrogen); after treatment at 2 $H_2O$— at 5.67 ppm doublet J=5 Hz (7-hydrogen).

IR Spectrum (nujol): Absorption at 1770 cm$^{-1}$ (β-lactam); at 1667 cm$^{-1}$ (amide carbonyl); at 2102 cm$^{-1}$ ($N_3$ and COO−); at 1600–1535 cm$^{-1}$ (C=C).

U.V. Spectrum (N/10 HCl in ethanol): Inflex. towards 222 nm: $E_1^1$=325; Max. at 261 nm: $E_1^1$=319; Inflex. towards 280 nm: $E_1^1$=271.

EXAMPLE 6

Internal salt of syn isomer of 3-[(2-methyl-1,3,4-thiadiazol-5-yl)-thiomethyl]-7-[2-(2-amino-4-thiazolyl)-2-(2-aminoiminomethylthioethoxyimino)-acetamido]-ceph-3-eme-4-carboxylic acid STEP A: Internal salt of syn isomer of 3-[(2-methyl-1,3,4-thiadiazol-5-yl)-thiomethyl]-7-[2-(2-tritylamino-4-thiazolyl)-2-(2-aminoiminomethylthioethoxyimino)-acetamido]-ceph-3-eme-4-carboxylic acid A mixture of 207 mg of 3-[(2-methyl-1,3,4-thiadiazol-5-yl)-thiomethyl]-7-amino-ceph-3-eme-4-carboxylic acid and 1.8 ml of dimethylformamide was stirred for 30 minutes and 90 mg of triethylenediamine and then 252 mg of pyridine hydroiodide were added thereto in fractions at 15° C. A solution of 318 mg of 2-(2-tritylamino-4-thiazolyl)-2-(2-aminoiminothiomethylethoxyimino)-acetic acid, 252 mg of pyridine hydroiodide and 1.8 ml of dimethylformamide were added all at once to the reaction mixture and then 252 mg of dicyclohexylcarbodiimide were added thereto. The mixture was stirred at 15° C. for 15 minutes and at 20° C. for 30 minutes and was then vacuum filtered. 120 ml of water were added to the filtrate and the mixture was stirred for 15 minutes and was vacuum filtered. The product was washed with water and dried to obtain 361 mg of raw product. The latter and 20 ml of methylene chloride were stirred for 30 minutes and was vacuum filtered. The filtrate was evaporated to dryness and the residue was taken up in chloroform. The solution was treated with activated carbon and was vacuum filtered. The filtrate was evaporated to dryness under argon to obtain 171 mg of internal salt of syn isomer of 3-[(2-methyl-1,3,4-thiadiazol-5-yl)-thiomethyl]-7-[2-(2-tritylamino-4-thiazolyl)-2-(2-aminoiminomethylthioethoxyimino)-acetamido]-ceph-3-eme-4-carboxylic acid.

IR Spectrum (nujol): Absorption at 1764 cm$^{-1}$ (β-lactam); at 1667 cm$^{-1}$ (amide); at 1599 and 1497 cm$^{-1}$ (aromatic and COO−); at 1526 and 1511 cm$^{-1}$ (amide II and heterocycle).

U.V. Spectrum (N/10 HCl in ethanol): Max. at 271 nm: $E_1^1$=227, ε=19,500.

STEP B: Internal salt of syn isomer of 3-[(2-methyl-1,3,4-thiadiazol-5-yl)-thiomethyl]-7-[2-(2-amino-4-thiazolyl)-2-(2-aminoiminomethylthioethoxyimino)-acetamido]-ceph-3-eme-4-carboxylic acid A mixture of 171 mg of the product of Step A and 1.71 ml of 92% trifluoroacetic acid was heated at 48°-50° C. with stirring for 2½ hours and the mixture was filtered. 30 ml of isopropyl ether were added to the filtrate and the mixture was stirred for 15 minutes, stood for 15 minutes and was vacuum filtered. The recovered product was washed with isopropyl ether and with ether and dried to obtain 93 mg of internal salt of syn isomer of 3-[(2-methyl-1,3,4-thiadiazol-5-yl)-thiomethyl]-7-[2-(2-amino-4-thiazolyl)-2-(2-aminoiminomethylthioethoxyimino)-acetamido]-ceph-3-eme-4-carboxylic acid melting at ≃260° C.

NMR Spectrum $(CD_3)_2SO$: Peaks at 2.67 ppm singulet ($\underline{CH}_3$—C=); at 4.33 ppm (N—O$\underline{CH}_2$— and 3-$\underline{CH}_2S$); at 5.0 to 5.83 ppm (6- and 7-hydrogens); at 6.78 ppm singulet (5-hydrogen of thiazole).

IR Spectrum (nujol): Absorption at 1760 cm$^{-1}$ (β-lactam); at 1660 cm$^{-1}$ (amide); at 1613–1595 cm$^{-1}$ (COO−); at 1531 cm$^{-1}$ (amide II + heterocycle).

U.V. Spectrum (N/10 HCl in ethanol): Inflex. towards 220 nm: $E_1^1$=312; Max. at 265 nm: $E_1^1$=307; Inflex. towards 280 nm: $E_1^1$=278.

EXAMPLE 7

Syn isomer of 3-acetoxymethyl-7-[2-(2-amino-4-thiazolyl)-2-(2-thiocyanatoethoxyimino)-acetamido]-ceph-3-eme-4-carboxylic acid STEP A: 2-(2-tritylamino-4-thiazolyl)-2-(2-thiocyanatoethoxyimino)-acetic acid A mixture of 6.83 g of the syn isomer of 2-(2-tritylamino-4-thiazolyl)-2-(2-iodoethoxyimino)-acetic acid solvated with dichloroethane, 7.61 g of ammonium thiocyanate and 35 ml of dimethylacetamide was stirred at 15° C. for 139 hours in the dark and the solution was placed in an ice water bath. 400 ml of distilled water and then 150 ml of an aqueous saturated sodium chloride solution were added to the reaction mixture and the mixture was stirred for 2 hours and was vacuum filtered. The product was washed with water and dried to obtain 4.55 g of product which was crystallized twice from ethyl acetate to obtain 3.44 g of 2-(2-tritylamino-4-thiazolyl)-2-(2-thiocyanatoethoxyimino)-acetic acid melting at 194° C.

STEP B: Syn isomer of benzhydryl 3-acetoxymethyl-7-[2-(2-tritylamino-4-thiazolyl)-2-(2-thiocyanatoethoxyimino)-acetamido]-ceph-3-eme-4-carboxylate A mixture of 1.69 g of the product of Step A, 0.685 g of pyridine hydroiodide, 1.16 g of benzhydryl 3-acetoxymethyl-7-amino-ceph-3-eme-4-carboxylate and 1.36 g of dicyclohexylcarbodiimide was admixed with 17 ml of dimethylformamide and the mixture was cooled to 16° C. for 30 minutes and was then vacuum filtered. 400 ml of ether were added to the filtrate and the mixture was stirred for 5 minutes and allowed to stand for one hour. The mixture was decanted and the gum was washed with ether and was added to 50 ml of ether. The mixture was kneaded until concretization and was vacuum filtered. The product was washed with ether and dried to obtain 1.92 of raw product which was chromatographed over silica gel. Elution with a 91-9 chloroform-acetonitrile mixture yielded 790 mg of amorphous syn isomer of benzhydryl 3-acetoxymethyl-7-[2-(2-tritylamino-4-thiazolyl)-2-(2-thiocyanatoethoxyimino)-acetamido]-ceph-3-eme-4-carboxylate NMR Spectrum $(CDCl_3)$: Peaks at 2.0 ppm singulet (—OAc); at 3.17 to 3.65 ppm (C$\underline{H}_2$S—); at 4.58 ppm triplet J=6 Hz (N—O—$CH_2$); at 4.65–4.87 ppm and 4.98–5.2 ppm (C$\underline{H}_2$—OAc); at 6.77 ppm singulet (5-hydrogen of syn thiazole).

IR Spectrum $(CHCl_3)$: Absorption at 2156 cm$^{-1}$ (CN); at 1793 cm$^{-1}$ (β-lactam); at 1739–1733 cm$^{-1}$ (ester + OAc); at 1689 cm$^{-1}$ (amide).

U.V. Spectrum (N/10 HCl in ethanol): Max. at 267 nm: $E_1^1 = 209$, $\epsilon = 19,540$.

STEP C: Syn isomer of 3-acetoxymethyl-7-[2-(2-amino-4-thiazolyl)-2-(2-thiocyanatoethoxyimino)-acetamido]-ceph-3-eme-4-carboxylic acid A mixture of 445 mg of the product of Step A and 4.4 ml of trifluoroacetic acid was stirred for 3 minutes at room temperature and 44 ml of iced isopropyl ether were added thereto. The mixture was stirred for 5 minutes and was vacuum filtered. The product was rinsed with a 1-1 isopropylether-ether mixture and then with ether and was dissolved in 0.8 ml of methanol. 8 ml of ether were added to the solution to cause precipitation and the mixture was stirred for 10 minutes and was then vacuum filtered. The product was rinsed with ether and dried to obtain 199 mg of syn isomer of 3-acetoxymethyl-7-[2-(2-amino-4-thiazolyl)-2-(2-thiocyanatoethoxyimino)-acetamido]-ceph-3-eme-4-carboxylic acid melting at 200° C.

NMR Spectrum (CD$_3$)$_2$SO: Peaks at 2.03 ppm singulet (OAc); at 3.17 to 3.83 ppm (C$\underline{H}_2$S); at 6.82 ppm singulet (5-hydrogen of syn thiazole).

IR Spectrum (nujol): Absorption at 2153 cm$^{-1}$ (S—CN); at 1781 cm$^{-1}$ ($\beta$-lactam).

U.V. Spectrum (N/10 HCl in ethanol): Max. at 264 nm: $\epsilon = 18,900$.

EXAMPLE 8

Internal salt of syn isomer of 3-acetoxymethyl-7-[2-(2-amino-4-thiazolyl)-2-(2-iminohydrazinomethylthioethoxyimino)-acetamido]-ceph-3-eme-4-carboxylic acid STEP A: Tritylthiosemicarbazide 9.11 g of thiosemicarbazide and 27.9 g of trityl chloride were rapidly added with stirring to 100 ml of dimethylacetamide and then 13 ml of triethylamine were added dropwise to the mixture at 15° C. The mixture stood at 15° C. for one hour and the pH was adjusted to 7 by addition of triethylamine. The mixture was then poured into 2 liters of an ice-water mixture and after stirring the mixture for 30 minutes, the mixture was vacuum filtered. The product was washed with water and dried at 50° C. under reduced pressure to obtain 31.3 g of product melting at 194° C. A mixture of 29.3 g of the product and 90 ml of ethyl acetate was stirred for 30 minutes and was vacuum filtered. The recovered product was washed with ethyl acetate and dried to obtain 25.05 g of tritylthiosemicarbazide melting at 208° C.

NMR Spectrum (CDCl$_3$): Peaks at 5.08 ppm, 6.92 ppm and 6.33 ppm (mobile hydrogen); at $\simeq$7.33 ppm (hydrogen of trityl).

IR Spectrum (CHCl$_3$): Absorption at 3505 cm$^{-1}$ (=C=NH$_2$).

U.V. Spectrum (N/10 HCl in ethanol): Max. at 245 nm: $E_1^1 = 405$.

STEP B: Internal salt of syn isomer of 2-(2-tritylamino-4-thiazolyl)-2-(2-tritylhydrazinoiminomethylthio-ethoxyimino)-acetic acid A solution of 7.5 g of the syn isomer of 2-(2-tritylamino-4-thiazolyl)-2-(2-iodoethoxyimino)-acetic acid solvated with dichloroethane, 13.5 g of N-tritylthiosemicarbazide and 45 ml of anhydrous dimethylformamide was heated in the dark at 30°-32° C. for 65 hours and was then poured into 900 ml of water. The mixture was stirred for 10 minutes and 60 ml of an aqueous saturated sodium chloride solution were added thereto. After 20 minutes, the mixture was vacuum filtered and the product was washed with water and dried to obtain 18.14 g of product. 5 g of the product were chromatographed over silica gel and was eluted with an 85-15 chloroform-methanol mixture. The product was taken up in isopropyl ether and then dried to obtain 1.44 g of internal salt of syn isomer of 2-(2-tritylamino-4-thiazolyl)-2-(2-tritylhydrazino imino-methylthio ethoxyimino)-acetic acid melting at $\simeq$200° C.

NMR Spectrum (CDCl$_3$): Peaks at 5.87 ppm singulet (5-hydrogen of thiazole); at 4.33 ppm (N—O—C$\underline{H}_2$—); at 7.18-7.35 ppm (hydrogen of trityls); at 5.42 ppm (mobile hydrogen).

IR Spectrum (CHCl$_3$): Absorption at 3392 cm$^{-1}$ (NH).

U.V. Spectrum (N/10 HCl in ethanol): max. at 278 nm: $E_1^1 = 180$.

STEP B: Syn isomer of benzhydryl 3-acetoxymethyl-7-[2-(2-tritylamino-4-thiazolyl)-2-(2-tritylhydrazinoiminomethylthioethoxyimino)-acetamido]-ceph-3-eme-4-carboxylate hydroiodide A mixture of 513 mg of the product of Step B, 134 mg of pyridine hydroiodide, 268 mg of dicyclohexylcarbodiimide, 227 mg of 3-acetoxymethyl-7-amino-ceph-3-eme-4-carboxylic acid and 3 ml of anhydrous dimethylformamide was stirred at room temperature for 20 minutes and 10 ml of methylene chloride were added thereto. The mixture was vacuum filtered and the filtrate was evaporated to dryness under reduced pressure. The residue was stirred with 40 ml of isopropyl ether for 5 minutes and was decanted. The resin was taken up in 40 ml of a 1-1 isopropyl ether-ether mixture and was triturated and stirred for 20 minutes. The mixture was vacuum filtered and the recovered product was washed with isopropyl ether and dried to obtain 680 mg of syn isomer of benzhydryl 3-acetoxy-methyl-7-[2-(2-tritylamino-4-thiazolyl)-2-(2-tritylhydrazino-iminomethylthio-ethoxyimino)-acetamido]-ceph-3-eme-4-carboxylate hydroiodide melting at 162° C. (decomposition).

IR Spectrum (CHCl$_3$): Absorption at 3391 cm$^{-1}$ (NH); at 1782 cm$^{-1}$ (C=O); at 1736-1730 cm$^{-1}$ (ester and OAc); at 1594, 1576 and 1496 cm$^{-1}$ (aromatic).

STEP D: Internal salt of syn isomer of 3-acetoxymethyl-7-[2-(2-amino-4-thiazolyl)-2-(2-iminohydrazinomethylthio-ethoxyimino)-acetamido]-ceph-3-eme-4-carboxylic acid A mixture of 0.94 g of the product of Step C, 9.4 ml of formic acid and 4.7 ml of water was stirred at 50° C. for 45 minutes and the mixture was then cooled to room temperature and was vacuum filtered. The filtrate was evaporated to dryness and the residue was taken up in 9 ml of trifluoroacetic acid. The mixture was stirred for 4 minutes and was vacuum filtered and 90 ml of isopropyl ether were added to the filtrate. The mixture was stirred for 5 minutes and was vacuum filtered and the product was rinsed with isopropyl ether and taken up in a minimum of methanol. Ether was added to the solution to cause precipitation and the mixture was filtered to obtain 282 mg of raw product. 558 mg of the product were suspended in 7 ml of water and pyridine was added to the mixture to obtain a pH of 6.6. The mixture was filtered and the filtrate was evaporated to dryness under reduced pressure. The residue was triturated with 5 ml of ether and the mixture was vacuum filtered. The product was rinsed with ether to obtain 500 mg of product which was stirred with 5 ml of methanol for 10 minutes. The mixture was vacuum filtered and the product was empasted with ether to obtain 96 mg of internal salt of syn isomer of 3-acetoxymethyl-7-[2-(2-amino-4-thiazolyl)-2-(2-iminohydrazinomethylthio-ethoxyimino)-acetamido]-ceph-3-eme-4-carboxylic acid melting at 210° C. (decomposition). The mother liquors yielded another 66 mg of the same product.

NMR Spectrum (C D$_3$)$_2$SO: Peaks at 2.03 ppm singulet (OAc); at 4.25 ppm (N—O—C$\underline{H}_2$—); at 6.78 ppm singulet (5-hydrogen of thiazole).

U.V. Spectrum (N/10 HCl in ethanol): Max. at 262 nm: $E_1^1 = 301$, $\epsilon = 16,800$.

EXAMPLE 9

Syn isomer of 3-acetoxymethyl-7-[2-(2-amino-4-thiazolyl)-2-difluoromethoxyimino-acetamido]-ceph-3-eme-4-carboxylic acid STEP A: Syn isomer of ethyl 2-(2-tritylamino-4-thiazolyl)-2-difluoromethoxy-imino-acetate A mixture of 3 g of the syn isomer of ethyl 2-hydroxyimino-2-(2-tritylamino-4-thiazolyl)-acetate hydrochloride, 20 ml of 2 N sodium hydroxide and 20 ml of 100% ethanol was stirred for 5 minutes during which a sodium salt precipitated and 60 ml of dioxane were added to dissolve the sodium salt. Monochlorodifluoromethane was bubbled through the mixture with good stirring for 30 minutes and 20 ml of 2 N sodium hydroxide, 20 ml of 100% ethanol and 60 ml of dioxane were added thereto. The bubbling was continued for 3 minutes and then 6.7 g of sodium bicarbonate were added thereto. The mixture was stirred at room temperature for 15 minutes and was vacuum filtered and the filtrate was reduced to a consistency of a syrup under reduced pressure at a temperature less than 40° C. The syrup was diluted with chloroform and was decanted. The organic phase was washed one with water, then with aqueous saturated sodium chloride solution, dried and evaporated to dryness. The residue was chromatographed over silica gel and was eluted with benzene to obtain 652 mg of syn isomer of ethyl 2-(2-tritylamino-4-triazolyl)-2-difluoromethoxy-imino-acetate in the form of a white resin.

NMR Spectrum (CDCl$_3$): Peaks at 5.55–6.75–7.95 ppm (C$\underline{H}$F$_2$); at 6.77 ppm singulet (5-hydrogen of syn thiazole).

U.V. Spectrum (ethanol): Max. at 308 nm: $E_1^1 = 80$, $\epsilon = 4,100$.

IR Spectrum: Absorption at 1141 cm$^{-1}$ (C=NOR); at 1145 cm$^{-1}$–1117 cm$^{-1}$ (CHF$_2$).

STEP B: Syn isomer of 2-(2-tritylamino-4-thiazolyl)-2-difluoromethoxyimino-acetic acid A mixture of 51 mg of the product of Step A, 0.05 ml of dioxane, 0.35 ml of 100% ethanol and 0.1 ml of N sodium hydroxide solution was stirred during which a slight gum formed which was dissolved by the addition of 0.1 ml of 100% ethanol. The mixture was hermetically sealed and was heated at 40° C. for 2½ hours and then stood overnight at room temperature with good stirring. The mixture was vacuum filtered and the recovered product was rinsed with a few drops of a 1–7 dioxane-ethanol mixture and then with ether to obtain 25 mg of a sodium salt. The latter was taken up in 1 ml of chloroform and 1 ml of water and N hydrochloric acid was added thereto until the pH was 2. The mixture was vigorously stirred and the decanted chloroform phase was washed with water, dried and evaporated to dryness to obtain 16 mg of syn isomer of 2-(2-tritylamino-4-thiazolyl)-2-difluoromethoxyimino-acetic acid in the form of a white resin.

NMR Spectrum (C$_2$DCl$_3$): Peaks at 5.4–6.6–7.8 ppm (C$\underline{H}$F$_2$); at 6.72 ppm singulet (5-hydrogen of syn thiazole); 9.33 and 10.25 ppm (OH+NH).

STEP C: Syn isomer of tert.-butyl 3-acetoxymethyl-7-[2-(2-tritylamino-4-thiazolyl)-2-difluoromethoxyimino]-acetamido-ceph-3-eme-4-carboxylate 2 ml of chloroform solution containing 309 mg of dicyclohexylcarbodiimide were added dropwise to a mixture of 820 mg of the product of Step B, 492 mg of tert-butyl 3-acetoxymethyl-7-amino-ceph-3-eme-4-carboxylate and 16 ml of chloroform in an ice bath and the mixture stood at room temperature for one hour and was then vacuum filtered. The filtrate was evaporated to dryness under reduced pressure and the residue was chromatographed over silica gel. Elution with a 94-6 methylene chloride-ethyl acetate mixture yielded 574 mg of syn isomer of tert.-butyl 3-acetoxymethyl-7-[2-(2-tritylamino-4-thiazolyl)-2-difluoromethoxyimino]-acetamido-ceph-3-eme-4-carboxylate in the form of a white resin.

NMR Spectrum (CDCl$_3$): Peaks at 1.54 ppm singulet (tert.-butyl); at 2.0 ppm singulet (OAc); at 5.6–6.8–8.0 ppm (C$\underline{H}$F$_2$); at 6.92 ppm singulet (5-hydrogen of syn thiazole).

U.V. Spectrum (N/10 HCl in ethanol): Max. at 262 nm: $E_1^1 = 217$.

STEP D: Syn isomer of 3-acetoxymethyl-7-[2-(2-amino-4-thiazolyl)-2-difluoromethoxyimino-acetamido]-ceph-3-eme-4-carboxylic acid A mixture of 0.32 g of the product of Step C and 1.6 ml of trifluoroacetic acid was stirred at room temperature for 3 minutes and was then poured into 16 ml of a 1-1 iced isopropyl ether-ether mixture. The mixture was stirred for 15 minutes and was vacuum filtered and the recovered product was rinsed with a mixture of ether and isopropyl ether and then with ether and dried to obtain 130 mg of white syn isomer of 3-acetoxymethyl-7-[2-(2-amino-4-thiazolyl)-2-difluoromethoxyimino-acetamido]-ceph-3-eme-4-carboxylic acid melting at ≃176° C. (decomposition).

NMR Spectrum (CD$_3$)$_2$SO: Peaks at 2.03 ppm singulet (OAc); at 5.95–7.13–8.23 ppm (C$\underline{H}$F$_2$); at 7.05 ppm singulet (5-hydrogen of syn thiazole).

U.V. Spectrum (N/10 HCl in ethanol): Max. at 278 nm: $E_1^1 = 265$.

IR Spectrum (Nujol): Absorption at 1777 cm$^{-1}$ ($\beta$–lactam); at 1726 cm$^{-1}$ (OAc); at 1031 cm$^{-1}$ (—C=NOR).

EXAMPLE 10

Injectable solutions were prepared containing 500 mg of either the syn isomer of 3-acetoxymethyl-7-[2-(2-amino-4-thiazolyl)-2-(2-aminoiminomethythioethoxyimino)-acetamido]-ceph-3-eme-4-carboxylic acid or the syn isomer of 3-acetoxymethyl-7-[2-(2-amino-4-thiazolyl)-2-difluoromethoxyimino-acetamido]-ceph-3-eme-4-carboxylic acid and sufficient sterile water excipient for a final volume of 5 ml.

Gelules were prepared containing 250 mg of either the syn isomer of 3-acetoxymethyl-7-[2-(2-amino-4-thiazolyl)-2-(2-aminoiminomethylthioethoxyimino)-acetamido]-ceph-3-eme-4-carboxylic acid or the syn isomer of 3-acetoxymethyl-7-[2-(2-amino-4-thiazolyl)-2-difluoromethoxyimino-acetamido]-ceph-3-eme-4-carboxylic acid and sufficient gelule excipient for a final weight of 400 mg.

PHARMACOLOGICAL DATA

A. In Vitro Activity

The method used was a dilution of a liquid medium where a series of tubes received the same quantity of a sterile nutritive media and increasing doses of the test compounds were placed therein. Then each tube was seeded with a bacterial strain and was incubated for 24 to 48 hours at 37° C. in an oven. The increasing inhibition was determined by transillulumination to determine the minimum inhibiting concentration (MIC in µg/ml and the results are reported in the following Tables.

PRODUCT OF EXAMPLE 1

| STRAINS | MIC in µg/ml | |
|---|---|---|
| | 24 H | 48 h |
| Staphylococcus aureus ATCC 6 538 Pen-Sensitive | 2 | 2 |
| Staphylococcus aureus UC 1 128 Pen-resistant | 2 | 3 |
| Staphylococcus aureus exp.n°54 146 | 2 | 2 |
| Streptococcus pyogenes A 561 | 0.02 | 0.02 |
| Bacillus subtilis ATCC 6 633 | 1 | 1 |
| Escherichia Coli Sensitive Tetracycline ATCC 9 637 | 1 | 1 |
| Escherichia Coli Resistant Tetracycline ATCC 11 303 | 0.05 | 0.05 |
| Escherichia Coli Exp. TO$_{26}$B$_6$ | 0.5 | 0.5 |
| Escherichia Coli Resistant Gentamycine, Tobramycine R 55 123 D | 0.5 | 0.5 |
| Klebsiella pneumoniae Exp. 52 145 | 0.5 | 0.5 |
| Klebsiella pneumoniae 2 536 Resistant Gentamycine | 1 | 2 |
| Proteus mirabilis (indol-) A 235 | 0.1 | 0.1 |
| Salmonella typhimurium 420 | 0.5 | 0.5 |
| Enterobacter cloacae 681 | 2 | 2 |
| Providencia Du 48 | 2 | 3 |
| Pseudomonas 8951 Resistant Gentamycine Tetracycline | 20 | 20 |
| Serratia Resistant Gentamycine 2 532 | 0.5 | 0.5 |

PRODUCT OF EXAMPLE 4

| STRAINS | MIC in µg/ml | |
|---|---|---|
| | 24 H | 48 H |
| Staphylococcus aureus ATCC 6 538 Pen-Sensitive | 1 | 2 |
| Staphylococcus aureus UC 1 128 Pen-Resistant | 2 | 2 |
| Staphylococcus aureus exp. n°54 146 | 2 | 2 |
| Streptococcus pyogenes A 561 | 0.05 | 0.05 |
| Bacillus subtillus ATCC 6 633 | 0.5 | 2 |
| Escherichia Coli Sensitive Tetracycline ATCC 9 637 | 2 | 2 |
| Escherichia Coli Resistant Tetracycline ATCC 11 303 | 0.2 | 0.2 |
| Escherichia Coli Exp. TO$_{26}$B$_6$ | 1 | 1 |
| Escherichia Coli Resistant Gentamycine, Tobramycine R 55 123 D | 1 | 1 |
| Klebsiella pneumoniae Exp. 52 145 | 1 | 1 |
| Klebsiella pneumoniae 2 536 Resistant Gentamycine | 5 | 5 |
| Proteus mirabilis (indol-) A 235 | 0.2 | 0.5 |
| Salmonella typhimurium 420 | 2 | 2 |
| Enterobacter cloacae 681 | 3 | 3 |
| Pseudomonas 3935 Exp. Sensible Gentamycine | 10 | 20 |
| Providencia Du 48 | 5 | 10 |
| Serratia Resistant Gentamycine 2 532 | 1 | 1 |

PRODUCT OF EXAMPLE 5

| STRAINS | MIC in µg/ml | |
|---|---|---|
| | 24 H | 48 H |
| Staphylococcus aureus ATCC 6 538 Pen-Sensitive | 1 | 1 |
| Staphylococcus aureus UC 1 128 Pen-Resistant | 1 | 2 |
| Staphylococcus aureus exp.N°54 146 | 1 | 2 |
| Streptococcus pyogenes A 561 | <0.02 | 0.05 |
| Bacillus subtilis ATCC 6 633 | 2 | 3 |
| Escherichia Coli Sensitive Tetracycline ATCC 9 637 | 2 | 2 |
| Escherichia Coli Resistant Tetracycline ATCC 11 303 | 0.2 | 0.2 |
| Escherichia Coli Exp. TO$_{26}$B$_6$ | 0.5 | 0.5 |
| Escherichia Coli Resistant Gentamycine, Tobramycine R 55 123 D | 1 | 1 |
| Klebsiella pneumoniae Exp. 52 145 | 1 | 1 |
| Klebsiella pneumoniae 2 536 Resistant Gentamycine | 2 | 3 |
| Proteus mirabilis (indol-) A 235 | 0.2 | 0.2 |
| Salmonella typhimurium 420 | 1 | 1 |
| Enterobacter cloacae 681 | 3 | 3 |
| Providencia Du 48 | 10 | 10 |
| Serratia Resistant Gentamycine 2 532 | 1 | 1 |

PRODUCT OF EXAMPLE 6

| STRAINS | MIC in µg/ml | |
|---|---|---|
| | 24 H | 48 H |
| Staphylococcus aureus ATCC 6 538 Pen-Sensitive | 1 | 2 |
| Staphylococcus aureus UC 1 128 Pen-Resistant | 2 | 2 |
| Staphylococcus aureus exp.n°54 146 | 2 | 2 |
| Streptococcus pyogenes A 561 | 0.05 | 0.05 |
| Bacillus subtilis ATCC 6 633 | 1 | 2 |
| Escherichia Coli Sensitive Tetracycline ATCC 9 637 | 5 | 5 |
| Escherichia Coli Resistant Tetracycline ATCC 11 303 | 0.1 | 0.1 |
| Escherichia Coli Exp. TO$_{26}$B$_6$ | 2 | 2 |
| Escherichia Coli Resistant Gentamycine, Tobramycine R 55 123 D | 1 | 1 |
| Klebsiella pneumoniae Exp. 52 145 | 1 | 1 |
| Klebsiella pneumoniae 2 536 Resistant Gentamycine | 5 | 5 |
| Proteus mirabilis (indol-) A 235 | 1 | 1 |
| Salmonella typhimurium 420 | 2 | 3 |
| Enterobacter cloacae 681 | 10 | 10 |
| Serratia Resistant Gentamycine 2 532 | 2 | 3 |

PRODUCT OF EXAMPLE 7

| STRAINS | MIC in µg/ml | |
|---|---|---|
| | 24 H | 48 H |
| Staphylococcus aureus ATCC 6 538 Pen-Sensitive | 1 | 1 |
| Staphylococcus aureus UC 1 128 Pen-Resistant | 1 | 1 |
| Staphylococcus aureus exp.N°54 146 | 1 | 2 |
| Streptococcus pyogenes A 561 | 0.02 | 0.02 |
| Bacillus subtilis ATCC 6 633 | 1 | 2 |
| Escherichia Coli Sensitive Tetracycline ATCC 9 637 | 5 | 5 |
| Escherichia Coli Resistant Tetracycline ATCC 11 303 | 0.2 | 0.2 |
| Escherichia Coli Exp. TO$_{26}$B$_6$ | 2 | 2 |
| Escherichia Coli Resistant Gentamycine R 55 123 D | 1 | 1 |
| Klebsiella pneumoniae Exp.52 145 | 0.5 | 0.5 |
| Klebsiella pneumoniae 2 536 Resistant Gentamycine | 5 | 5 |
| Proteus mirabilis (indol-) A 235 | 0.2 | 0.5 |
| Salmonella typhimurium 420 | 1 | 3 |

PRODUCT OF EXAMPLE 7 -continued

| STRAINS | MIC in μg/ml | |
|---|---|---|
| | 24 H | 48 H |
| Providencia Du 48 | 10 | 10 |
| Serratia Resistant Gentamycine 2 532 | 2 | 3 |

PRODUCT OF EXAMPLE 8

| STRAINS | MIC in μg/ml | |
|---|---|---|
| | 24 H | 48 H |
| *Staphylococcus aureus* ATCC 6 538 Pen-Sensitive | 1 | 2 |
| *Staphylococcus aureus* UC 1 128 Pen-Resistant | 2 | 2 |
| *Staphylococcus aureus* exp.N°54 146 | 1 | 2 |
| *Streptococcus pyogenes* A 561 | 0.02 | 0.05 |
| *Bacillus subtilis* ATCC 6 633 | 1 | 3 |
| *Escherichia Coli* Sensitive Tetracycline ATCC 9 637 | 2 | 2 |
| *Escherichia Coli* Resistant Tetracycline ATCC 11 303 | 0.5 | 0.5 |
| *Escherichia Coli* Exp. $TO_{26}B_6$ | 1 | 1 |
| *Escherichia Coli* Resistant Gentamycine, Tobramycine R 55 123 D | 1 | 1 |
| *Klebsiella pneumoniae* Exp. 52 145 | 1 | 1 |
| *Klebsiella pneumoniae* 2 536 Resistant Gentamycine | 5 | 10 |
| *Proteus mirabilis* (indol-) A 235 | 0.2 | 0.2 |
| *Salmonella typhimurium* 420 | 1 | 2 |
| Serratia Resistant Gentamycine 2 532 | 1 | 2 |

OF EXAMPLE 9

| STRAINS | MIC in μg/ml | |
|---|---|---|
| | 24 H | 48 H |
| *Staphylococcus aureus* ATCC 6 538 Pen-Sensitive | 1 | 1 |
| *Staphylococcus aureus* UC 1 128 Pen-Resistant | 1 | 2 |
| *Staphylococcus aureus* exp.n°54 146 | 1 | 2 |
| *Streptococcus pyogenes* A 561 | 0.05 | 0.05 |
| *Streptococcus faecalis* 5 432 | 5 | — |
| *Bacillus subtilis* ATCC 6 633 | 1 | 5 |
| *Escherichia Coli* Sensitive Tetracycline ATCC 9 637 | 0.5 | 1 |
| *Escherichia Coli* Resistant Tetracycline ATCC 11 303 | 0.05 | 0.1 |
| *Escherichia Coli* Exp.$TO_{26}B_6$ | 0.2 | 0.2 |
| *Escherichia Coli* Resistant Gentamycine, Tobramycine R 55 123 D | 0.2 | 0.2 |
| *Klebsiella pneumoniae* Exp.52 145 | 0.05 | 0.05 |
| *Klebsiella pneumoniae* 2 536 Resistant Gentamycine | 0.5 | 0.5 |
| *Proteus mirabilis* (indol-) A 235 | 0.05 | 0.05 |
| *Salmonella typhimurium* 420 | 0.5 | 0.05 |
| Providencia Du 48 | 2 | 2 |
| Serratia Resistant Gentamycine 2 532 | 0.5 | 0.5 |

B. Experimental Infection with Escherichia coli $TO_{26}B_6$

The product of Example 1 was studied for its activity against an experimental infection of Escherichia coil in groups of 10 male mice weighing about 21.5 g. The mice received an intraperitoneal injection of 0.5 ml of a 24 hour old culture in a nutritive media of Escherichia Coli $TO_{26}B_6$ of the Pasteur Institute diluted 1/5 with distilled water. The test product was administered subcutaneously 1 hour and 5 and 24 hours after the infection and the number of dead was determined after 8 days. The results are reported in the following Table.

| Doses in mg | MORTALITY AFTER HOURS | | | | | | No. of mice surviving 8th day |
|---|---|---|---|---|---|---|---|
| | 7H | 7H15 | 21H30 | 24 H | 28 H | 36 H | |
| Control | 1 | 1 | 8 | | | | 0/10 |
| 0.1 | | | | 1 | 1 | 1 | 6/10 |
| 0.25 | | | | | | | 10/10 |

C. Experimental Infection of Proteus Mirabilis

Groups of 10 mice with an average weight of 21.5 g received intraperitoneally 0.5 ml of a 24 hour old culture in oxoid bouillon of Proteus mirabilis A 235 diluted 1/10 with distilled water. The mice then received subcutaneously the compound of Example 1 one hour and 5 and 24 hours after the infection and the results are reported in the following Table.

| Dose in mg | MORTALITY AFTER HOURS | | | | Mice surviving on 8th day |
|---|---|---|---|---|---|
| | 21H15 | 23H45 | 25 H | 31 H | |
| Controls | 9 | 1 | | | 0/10 |
| 0.025 | | 1 | 1 | 1 | 7/10 |
| 0.05 | | | | | 10/10 |
| 0.1 | | | | | 10/10 |
| 0.25 | | | | | 10/10 |
| 0.5 | | | | | 10/10 |

D. Experimental infection of Proteus Morganii A236

The activity of the product of Example 1 against an experimental infection of Proteus Morganii A236 was determined in groups of 10 mice weighing an average of 20.5 g which were infected by intraperitoneal injection of 0.5 ml of a culture thereof in a medium with a pH of 7 diluted to one tenth. The test compound was cutaneously administered 1,5 and 24 hours after the injection and the results are reported in the following Table.

| Dose in mg | MORTALITY AFTER HOURS | | | | | Mice surviving on 8th day |
|---|---|---|---|---|---|---|
| | 4H | 6H | 6H15 | 21H10 | 45H20 | |
| Controls | 10 | | | | | 0/10 |
| 0,05 | 1 | 2 | 1 | 3 | 1 | 2/10 |
| 0,1 | | | | | | 10/10 |
| 0,25 | | | | | | 10/10 |
| 0,5 | | | | | | 10/10 |

E. Experimental infection of Klebsiella Pneumoniae

The activity of the compound of Example 1 against an experimental infection of Klebsiella Pneumonia No. 52,145 was determined on groups of 10 mice having an average weight of 21 g by intraperitoneal injection of 0.5 ml of a culture thereof with a pH of 6 diluted to 1/1500. The test compound was administered by injection 1,5 and 24 hours after the infection and the results are reported in the following Table.

| Dose in mg | MORTALITY AFTER HOURS | | | | | | | | | Mice surviving on 8th day |
|---|---|---|---|---|---|---|---|---|---|---|
| | 30H | 45H30 | 45H45 | 49H | 70H | 4 J | 5 J | 6 J | 8 J | |
| Controls | 1 | 6 | 1 | 1 | 1 | | | | | 0/10 |
| 0,1 | | | | | | 1 | 1 | 1 | 1 | 6/10 |
| 0,25 | | | | | | | 1 | 1 | | 8/10 |
| 0,5 | | | | | | | | 1 | | 9/10 |
| 1 | | | | | | | | | | 10/10 |

-continued

| Dose in mg | MORTALITY AFTER HOURS | | | | | | | | Mice surviving on 8th day |
|---|---|---|---|---|---|---|---|---|---|
| | 30H | 45H30 | 45H45 | 49H | 70H | 4 J | 5 J | 6 J | 8 J | |
| 1,5 | | | | | | | | | | 10/10 |

Various modifications of the products and processes of the invention may be made without departing from the spirit or scope thereof and it should be understood that the invention is to be limited only as defined in the appended claims.

We claim:

1. A compound selected from the group consisting of a syn isomer of a compound of the formula

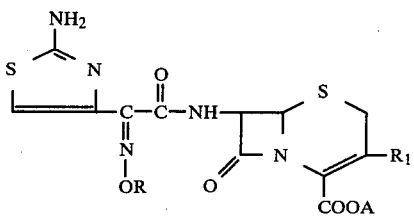

wherein R is selected from the group consisting of —(CH₂)ₙ—S—R₂, —CHF₂ and —(CH₂)ₙ—S—CN, R₂ is selected from the group consisting of optionally protonated

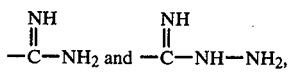

n is an integer from 1 to 4, R₁ is selected from the group consisting of hydrogen, chloro, methoxy, alkyl and alkylthio of 1 to 5 carbon atoms, cycloalkyl of 3 to 5 carbon atoms, azidomethyl, acetoxymethyl, carbamoyloxymethyl,

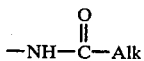

and —CH₂—S—R', Alk is alkyl of 1 to 4 carbon atoms, R' is selected from the group consisting of an acyl of an aliphatic acid of 2 to 4 carbon atoms and a member selected from the group consisting of 1,2,3-thiadiazolyl, 1,2,5-thiadiazolyl, 1,2,4-thiadiazolyl, 1,3,4-thiadiazolyl, 1-H-tetrazolyl, 1,3-thiazolyl, 1,2,3-triazolyl, 1,2,4-triazolyl, 1,3,4-triazolyl, 1,2,3-oxadiazolyl, 1,2,4-oxadiazolyl, 1,2,5-oxadiazolyl and 1,3,4-oxadiazolyl optionally substituted with at least one member of the group consisting of methyl, ethyl, propyl, isopropyl, methoxy, ethoxy, propoxy, isopropoxy, amino, hydroxycarbonylmethyl, dimethylaminoethyl and diethylaminoethyl, A is selected from the group consisting of hydrogen and an easily cleavable ester and when R is —(CH₂)ₙ—SR₂, the group COOA may be the anion —COO⁻ and when R is —(CH₂)—SCN or CHF₂, A may further be selected from the group consisting of an equivalent of an alkali metal, an alkaline earth metal, magnesium, —NH₄ and a non-toxic, pharmaceutically acceptable organic amine and their non-toxic, pharmaceutically acceptable acid addition salts.

2. A compound of claim 1 wherein R₁ is selected from the group consisting of hydrogen, acetoxymethyl, azidomethyl and —CH₂S-R" and R" is selected from the group consisting of 1-methyl-1(H)-tetrazolyl and 2-methyl-1,3,4-thiadiazolyl.

3. A compound of claim 2 wherein R is selected from the group consisting of —CHF₂ and

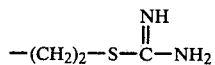

in an optionally protonated form.

4. A compound of claim 1 selected from the group consisting of the syn isomer of 3-acetoxymethyl-7-[2-(2-amino-4-thiazolyl)-2-(2-aminoiminomethylthio-ethoxyimino)-acetamido]-ceph-3-eme-4-carboxylic acid in the form of its internal salt, its easily cleavable esters and its non-toxic, pharmaceutically acceptable acid addition salts.

5. A compound of claim 1 selected from the group consisting of the syn isomer of 3-acetoxymethyl-7-[2-(2-amino-4-thiazolyl)-2-difluoromethoxyimino-acetamido]-ceph-3-eme-4-carboxylic acid, its easily cleavable esters, its alkali metal, alkaline earth metal, magnesium, —NH₄ and non-toxic, pharmaceutically acceptable organic amine salts and its non-toxic, pharmaceutically acceptable acid addition salts.

6. An antibiotic composition comprising an antibiotically effective amount of at least one compound of claim 1 and an inert pharmaceutical carrier.

7. A composition of claim 6 wherein R₁ is selected from the group consisting of hydrogen, acetoxymethyl, azidomethyl and —CH₂S-R" and R" is selected from the group consisting of 1-methyl-1(H)-tetrazolyl and 2-methyl-1,3,4-thiadiazolyl.

8. A composition of claim 6 wherein R is selected from the group consisting of -CHF₂ and

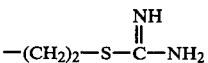

is an optionally protonated form.

9. A composition of claim 6 wherein the compound is selected from the group consisting of the syn isomer of 3-acetoxymethyl-7-[2-(2-amino-4-thiazolyl)-2-(2-aminoiminomethylthioethoxyimino)-acetamido]-ceph-3-eme-4-carboxylic acid in the form of its internal salt, or its easily cleavable esters and its non-toxic, pharmaceutically acceptable acid addition salts.

10. A composition of claim 6 wherein the compound is selected from the group consisting of the syn isomer of 3-acetoxymethyl-7-[2-(2-amino-4-thiazolyl)-2-difluoromethoxyimino-acetamido]-ceph-3-eme-4-carboxylic acid, its easily cleavable esters, it alkali metal, alkaline earth metal, magnesium, —NH₄ and non-toxic, pharmaceutically acceptable organic amine salts and its non-toxic, pharmaceutically acceptable acid addition salts.

11. A method of combatting bacterial infections in warm-blooded animals comprising administering to warm-blooded animals an antibacterially effective amount of at least one compound of claim 1.

12. A method of claim 11 wherein R₁ is selected from the group consisting of hydrogen, acetoxymethyl, azidomethyl and —CH₂S—R" and R" is selected from the group consisting of 1-methyl-1(H)-tetrazolyl and 2-methyl-1,3,4-thiadiazolyl.

13. A method of claim 11 wherein R is selected from the group consisting of -CHF$_2$ and

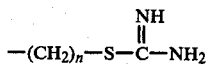

in an optionally protonated form.

14. A method of claim 11 wherein the compound is selected from the group consisting of the syn isomer of 3-acetoxymethyl-7-[2-(2-amino-4-thiazolyl)-2-(2-aminoiminomethylthioethoxyimino)-acetamido]-ceph-3-eme-4-carboxylic acid in the form of its internal salt, or its easily cleavable esters and its non-toxic, pharmaceutically acceptable acid addition salts.

15. A method of claim 11 wherein the compound is selected from the group consisting of the syn isomer of 3-acetoxymethyl-7-[2-(2-amino-4-thiazolyl)-2-difluoromethoxyimino-acetamido]-ceph-3-eme-4-carboxylic acid, its easily cleavable esters, its alkali metal, alkaline earth metal, magnesium, —NH$_4$ and non-toxic, pharmaceutically acceptable organic amine salts and its non-toxic, pharmaceutically acceptable acid addition salts.

* * * * *

UNITED STATES PATENT AND TRADEMARK OFFICE
CERTIFICATE OF CORRECTION

PATENT NO. : 4,328,225  Page 1 of 3
DATED : May 4, 1982
INVENTOR(S) : MICHEL VIGNAU and RENÉ HEYMÈS It is certified that error appears in the above—identified patent and that said Letters Patent is hereby corrected as shown below:

Column 2, line 29: "propionylix-" should be -- propionyloxy- --.
Column 2, line 30: "yethyl" should read -- ethyl --.
Column 2, line 31; Column 13, line 35; Column 14, line 22;
Column 18, line 44: "acetox-" should read -- acetoxy- --.
Column 2, line 32: "yheptyl" should read -- heptyl --.
Column 2, line 53; Column 11, line 30: "CH-" should be
    -- $CH_2$- --.
Column 2, line 54; Column 11, line 31: Delete "$_2$-".
Column 3, line 3; Column 15, line 15; Column 17, line 20;
Column 22, line 55: "aminoiminomethylthioethox-" should read
    -- aminoiminomethylthioethoxy- --.
Column 3, line 4; Column 15, line 16; Column 17, line 21;
Column 18, line 41; Column 19, line 18; Column 20, line 8;
Column 21, lines 4 and 21; Column 22, line 56; Column 28,
    line 17: "yimino" should read -- imino --.
Column 3, line 46: "Hal-" should read -- $Hal_1$- --.
Column 3, line 47: Delete "$_1$-".
Column 5, line 41: "benzylox-" should read -- benzyloxy- --.
Column 5, line 42; Column 6, line 31: "ycarbonyl" should
    read -- carbonyl --.
Column 5, line 62: "valerylox-" should read -- valeryloxy- --.
Column 5, line 63; Column 13, line 36; Column 14, line 23;
Column 18, line 45: "ymethyl" should read -- methyl --.

UNITED STATES PATENT AND TRADEMARK OFFICE
CERTIFICATE OF CORRECTION

PATENT NO. : 4,328,225

DATED : May 4, 1982

INVENTOR(S) : MICHEL VIGNAU and RENE HEYMES

It is certified that error appears in the above—identified patent and that said Letters Patent is hereby corrected as shown below:

Column 6, line 30: "butox-" should read -- butoxy- --.

Column 12, line 60: "iodoe-" should read -- iodo- --.

Column 12, line 61: "thoxy" should read -- ethoxy --.

Column 14, line 38: "aminoiminoethylthio-" should read
        -- aminoiminomethylthio- --.

Column 14, last line: "aminoiminoethylthioe-" should read
        -- aminoiminomethylthio- --.

Column 15, lines 1 and 30; Column 16, line 63: "thoxyimino"
        should read -- ethoxyimino --.

Column 15, line 29; Column 16, line 62: "aminoiminomethylthioe-"
        should read -- aminoiminomethylthio- --.

Column 16, line 39: "aminoiminomethylthi-" should read
        -- aminoiminomethylthio- --.

Column 16, line 40: "oethoxyimino" should read
        -- ethoxyimino --.

Column 18, lines 20 and 23: "thi-" should read -- thio- --.

Column 18, lines 21 and 24: "ocyanatoethoxyimino" should read
        -- cyanatoethoxyimino --.

Column 18, line 40; Column 19, line 17: "thiocyanatoethox- "
        should read -- thiocyanatoethoxy- --.

Column 19, line 62: "tritylthi-" should read -- tritylthio- --.

UNITED STATES PATENT AND TRADEMARK OFFICE
CERTIFICATE OF CORRECTION

PATENT NO. : 4,328,225

DATED : May 4, 1982

INVENTOR(S) : MICHEL VIGNAU and RENÉ HEYMÉS

It is certified that error appears in the above—identified patent and that said Letters Patent is hereby corrected as shown below:

Column 19, line 63: "osemicarbazide" should read
-- semicarbazide --.

Column 21, line 20; Column 27, line 58:
"hydrox-" should read -- hydroxy- --.

Column 25, in the Table "OF EXAMPLE 9" the values for
"Salmonella typhimurium 420" should be
-- 0.5      0.5 -- instead of "0.5    0.05".

Column 27, line 59: "ycarbonylmethyl" should be
-- carbonylmethyl --.

Column 28, line 16; Column 20, line 7; Column 21, line 3:
"ethox-" should read -- ethoxy- --.

Signed and Sealed this

Thirty-first Day of August 1982

[SEAL]

Attest:

GERALD J. MOSSINGHOFF

Attesting Officer

Commissioner of Patents and Trademarks